(12) United States Patent
Jackson et al.

(10) Patent No.: US 6,242,175 B1
(45) Date of Patent: Jun. 5, 2001

(54) METHODS AND MEANS RELATING TO RETROTRANSPOSON AND RETROVIRAL INTEGRATION

(75) Inventors: Stephen Philip Jackson, Cambridge; Jessica Anne Downs, Cambridgeshire, both of (GB)

(73) Assignee: KuDos Pharmaceuticals Limited, Cambridge (GB)

( * ) Notice: Subject to any disclaimer, the term of this patent is extended or adjusted under 35 U.S.C. 154(b) by 0 days.

(21) Appl. No.: 09/341,515

(22) PCT Filed: Jan. 13, 1998

(86) PCT No.: PCT/GB98/00099

§ 371 Date: Jul. 12, 1999

§ 102(e) Date: Jul. 12, 1999

(87) PCT Pub. No.: WO98/30903

PCT Pub. Date: Jul. 16, 1998

(30) Foreign Application Priority Data

Jan. 13, 1997 (GB) .................................................. 9700574

(51) Int. Cl.[7] ...................................................... C12Q 1/70
(52) U.S. Cl. .................................. 435/5; 424/94.1; 435/6; 435/70.1; 435/183; 435/530; 435/412; 435/536; 435/23.1
(58) Field of Search ................................ 424/94.1; 435/5, 435/6, 70.1, 183; 530/412; 536/23.1

(56) References Cited

FOREIGN PATENT DOCUMENTS

WO 94/17189   8/1994   (WO) .
WO 95/10288   4/1995   (WO) .

OTHER PUBLICATIONS

Gaken, et al., "Efficient Retroviral Infection of Mammalian Cells is Blocked by Inhibition of Poly (ADP–Ribose) Polymerase Activity," *Journal of Virology*, (Jun. 1996), vol. 70, No.6:3992–4000.

Kaczmarski, et al., "Lupus Autoantigen Ku Protein Binds HIV–1 TAR RNA in Vitro," *Biochem. and Biophys. Res. Comm.*, (Oct. 29, 1993), vol. 196, No. 2:935–942.

Salles, et al., "Rapid Quantification of DNA Repair Synthesis in Cell Extracts," *Analy. Biochem.*, (Jul. 14, 1993), vol. 215:304–306.

Troelstra et al., "Ku starts at the end." Current Biology vol. 4 (1994), p. 1149–1151.*

Anderson, C.W., "DNA damage and the DNA–activated protein kinase." Trends in Biochemical Sciences vol. 18 (1993), p. 433–437.*

Finnie et al., "DNA–dependent protein kinase activity is absent in xrs–6 cells: Implications for site specific recombination and DNA double strand break repair." Proceedings of the National Academy of Sciences, USA vol. 92 (1995), p. 320–324.*

Take et al., "OK1035, a selective inhibitor of DNA–pependent protein kinase." Biochemical and Biophysical Research Communications vol. 215 (1995), p. 41–47.*

Taccioli et al., "Ku*0: Product of the XRCC5 gene and its role in DNA repair and V(D)J recombination." Science vol. 265 (1994), p. 1442–1445.*

Stracher A.C., "Drug targeting and delivery, molecular principles of." in Molecular Biology and Biotechnology (VCH Publishers 1995) p. 260–262.*

* cited by examiner

Primary Examiner—Jeffrey Stucker
Assistant Examiner—Ulrike Winkler
(74) Attorney, Agent, or Firm—Pamela Sherwood; Bozicevic Field & Francis LLP (57) ABSTRACT

Ku(Ku70 and Ku80) of yeast and mammalian cells and other components of the Ku-associated DNA repair pathway are involved in retrotransposon and retroviral integration into cellular nucleic acids. Agents which inhibit activity of the pathway are useful for inhibition of retroviruses. Such agents are obtainable using assays involving the Ku-associated DNA repair pathway and one or more components thereof.

15 Claims, 5 Drawing Sheets

METHODS AND MEANS RELATING TO RETROTRANSPOSON AND RETROVIRAL INTEGRATION

CROSS-REFERENCE TO RELATED APPLICATIONS

This application is a §371 National Stage filing of International Patent application no. PCT/GB98/00099, filed Jan. 13, 1998, which claims priority to Great Britain patent application no. GB9700574.8, filed Jan. 13, 1997.

The present invention relates to the processes whereby retroviruses and retrotransposons (retroposons) insert their genetic material into the genome of a eukaryotic host cell in order to carry out a productive infection cycle. More specifically, it relates to proteins of the host cell that have now been found to be required for efficient retrotransposition, which are highly conserved throughout the eukaryotic kingdom but which are not required for cell functioning under most normal conditions. These proteins represent novel targets for anti-retroviral drugs. In addition, assay systems are provided with which anti-retroviral drugs can be screened and tested in vivo and in vitro.

The invention is based on the surprising discovery, contrary to prior teachings, that Ku-associated DNA repair mechanisms are involved in retrovirus and retrotransposon nucleic acid integration. Retrovirus and/or retrotransposon activity is shown by experimental work described herein to be inhibited in both yeast and mammalian cells where Ku function in the cells is reduced.

Retroviruses and Retrotransposons

Retroviruses are RNA viruses that must insert a DNA copy (cDNA) of their genome into the host chromosome in order to carry out a productive infection. When integrated, the virus is termed a provirus (Varmus, 1988). Some eukaryotic transposable DNA elements are related to retroviruses in that they transpose via an RNA intermediate. These elements, termed retrotransposons or retroposons, are transcribed into RNA, the RNA is copied into double-stranded (ds) DNA, then the dsDNA is inserted into the genome of the host cell.

The available evidence indicates that the integration of retroviruses and retrotransposons occurs through entirely analogous mechanisms, and that retroviruses can be viewed as retrotransposons with an extracellular phase of their life cycle. For example, the Ty1 and Ty5 retrotransposons of the yeast *Saccharomyces cerevisiae* have been shown to integrate into the host yeast genome by the same type of mechanism that is employed by mammalian retrotransposons and retroviruses to integrate into mammalian host cell DNA (Boeke et al., 1985; Garfinkel, 1985; Grandgenett and Mumm, 1990; Boeke and Sandmeyer, 1991).

Retroviruses are of considerable risk to human and animal health, as evidenced by the fact that retroviruses cause diseases such as acquired immune deficiency syndrome (AIDS; caused by human immunodeficiency virus; HIV-1), various animal cancers, and human adult T-cell leukaemia/lymphoma (Varmus, 1988); also retroviruses have been linked to a variety of other common disorders, including Type I diabetes and multiple sclerosis (Conrad et al., 1997; Perron et al. 1997 and Benoist and Mathis, 1997). In many but not all cases, cancer formation by certain retroviruses is a consequence of them carrying oncogenes. Furthermore, retroviral integration and retrotransposition can result in mutagenic inactivation of genes at their sites of insertion, or can result in aberrant expression of adjacent host genes, both of which can have deleterious consequences for the host organism. Retroviruses are also becoming used more and more commonly for gene delivery and are likely to play increasingly important roles in gene therapy. An understanding of how retroviruses function and how they can be controlled is therefore of great commercial and medical importance.

Over recent years, a vast amount of effort has been directed towards identifying inhibitors of retroviral infection because these agents have potential use in combatting retrovirally-borne diseases. To date, most drug development programmes have focused on virally-encoded products. However, given the short life cycle of retroviruses and their inherently high rates of genetic change, it is anticipated that a frequent problem with such strategies will be that drug resistant virus derivatives will arise through alterations of the virally-encoded target molecule (for example, Sandstrom and Folks, 1996 and references therein). Thus, most anti-retroviral drugs that interfere with virally-encoded proteins may only have a limited useful life-span. Another limitation of drugs that target virus proteins is that many will not have a broad applicability and will be inherently highly specific to a particular virus or even a certain strain of a particular virus.

Retroviral Integration

Given what is known about the retroviral life cycle, an attractive target for anti-retroviral therapeutics is to interfere with the integration of the viral cDNA into the host genome. Most importantly, this event is essential for efficient viral propagation (for example, Sakai et al., 1993; for reviews, see Varmus, 1988; Grandgenett and Mumm, 1990). In addition, since similar types of process are not believed to be essential for the functioning of most normally growing host cells, inhibitors of retroviral integration would not be expected to be particularly toxic to the host.

In light of these and other considerations, retroviral reverse transcriptases and integrases have been targeted for drug development. Although this has met with some success, high rates of genetic change by the targeted virus and variations between different viral strains is likely to limit the scope for anti-reverse transcriptase and anti-integrase drugs, particularly in the long term.

One way to surmount the problems outlined above would be to identify host cell proteins that are required for efficient retroviral integration and derive drugs that inhibit these molecules. First, it would be very difficult or impossible for the virus to mutate in such a way that it could evade drug action. Second, such host cell proteins would be expected to be necessary for the propagation of most retroviruses, meaning that drugs that interfere with them would be effective against a wide spectrum of retrovirus types.

Until now, the idea of there being a host factor (or host factors) that is required for retroviral integration but is not necessary for normal host cell growth seemed unlikely. This is because several lines of research have indicated that all the steps needed for covalently linking retrovirus or retrotransposon cDNA to the target DNA molecule can be performed in vitro by purified retroviral integrase protein (for example, Craigie et al., 1990; Bushman et al., 1990; Katz et al., 1990; Grandgenett and Mumm, 1990). In addition, although host factors have been conceived to help with viral integration, it was assumed that these would correspond to "housekeeping proteins" that are essential for host cell viability. Thus, if host "helper" proteins did exist, it was expected that inhibiting them with drugs would not be worthwhile in a therapeutic context because this would also kill the cells of the host.

In spite of these predictions, the present invention is surprisingly founded on the discovery that a series of host cell proteins are essential for efficient retrotransposon integration despite being unnecessary for host cell viability under most circumstances. These factors, which are components of a system termed the Ku-associated DNA repair apparatus, are therefore highly attractive targets for anti-retroviral therapy.

The Ku-Associated DNA Repair System

Previous work has revealed that the protein Ku is an essential component of the DNA repair apparatus in organisms ranging from humans, to *Drosophila melanogaster*, to *S. cerevisiae* (Jackson and Jeggo, 1995; Boulton and Jackson, 1996; Boulton and Jackson, 1996 and references therein). Specifically, the type of DNA repair process in which Ku is involved is termed illegitimate DNA end-joining or DNA double-strand break (DSB) repair. Since Ku binds to DNA DSBs in vitro, it has been proposed that Ku binds to DNA DSBs as they arise in vivo and helps to promote their efficient ligation. In addition, Ku is required for V(D)J recombination, a DNA "cut-and-paste" process that generates the antigen-binding molecules of the immune system of vertebrates (for reviews, see Lewis, 1994; Jackson and Jeggo, 1995).

In all organisms in which it has been identified, Ku exists as a heterodimer of two polypeptides of approximately 70 kDa (termed Ku70 in humans; Yku70p or Hdf1p in *S. cerevisiae*) and 80 kDa (Ku80 or Ku86 in humans; Yku80p or Hdf2p in *S. cerevisiae*). References for this are given below. Ku-defective cells are hypersensitive to killing by ionising radiation or by radiomimetic agents. However, in both yeast and mammalian systems, lack of Ku function has minimal or undetectable effects on cell viability and cell growth rates under normal conditions (Boulton and Jackson, 1996a, Milne et al., Blunt et al.; Jackson and Jeggo and references therein; Nussenzweig et al. and Zhu et al.).

Recently, additional components of the Ku-associated DNA repair pathway have been identified. One of these is the mammalian protein XRCC4, deficiencies in which produce defects in DSB repair and V(D)J recombination (Li et al., 1995). Others identified are the yeast factors Rad50p, Mre11p, and Xrs2p (see below) and the DNA ligase Lig4p (see below). Since human cells possess homologues of all these latter factors, they should function in DSB repair and related processes in essentially all eukaryotes.

Reeves and Sthoeger, and Chan et al. disclose cDNA and amino acid sequences of human Ku70. Cai et al. disclose chromosomal location and expression of the genes encoding Ku70 and Ku80 in human cell lines and normal tissues, while Yaneva et al. disclose the cDNA-derived amino acid sequence of human Ku80. Drosophila Ku (Yolk Protein Factor 1) is disclosed by Jacoby and Wensink. Feldmann and Winnaker, Milne et al., Beall et al., and Boulton and Jackson (1996a, 1996b) give sequence and functional information about yeast (*Saccharomyces cerevisiae*) Ku70 and Ku80.

Alani et al. discloses the nucleic acid and amino acid sequences of yeast RAD50. Human RAD50 and MRE11 are described in Dolganov et al. and Petrini et al., respectively. Ivanov et al. describes XRS2 of yeast.

Ku-associated DNA repair, which is an illegitimate DNA end repair mechanism, requires a discrete set of gene products (as discussed), and is a separate pathway from other DNA repair pathways which include homologous recombination repair, nucleotide excision repair, base excision repair and DNA mismatch repair.

Rationale For the Experimental Approach Adopted in Making the Present Invention

The present invention has been made by testing whether Ku plays a positive or negative role in the normal life cycle of retrotransposons, despite several lines of evidence suggesting that this is very unlikely to be the case.

One reason for the inventors' interest was that linear cDNA is generated as a intermediate during the life cycle of retroviruses and retrotransposons, raising the possibility that Ku may bind to it. The prevailing view, however, is that Ku will be unable to bind the viral cDNA, as this is assumed to be always associated tightly with virally-encoded factors. Nevertheless, since unpublished biochemical data from the inventors' laboratory indicate that Ku is able to bind to DNA ends with a tenacity almost unrivalled by any other characterised protein, it was felt that Ku gaining access to the retrotransposon cDNA could not be ruled out.

The second rationale for the investigations was the inventors' belief in a possibility that the host Ku-associated DNA DSB repair apparatus may play a role in retrovirus and retrotransposon integration. Although the retrotransposon or retrovirus integrase carries out all the steps needed to covalently link the cDNA to the target DNA molecule (for example, Craigie et al., 1990; Bushman et al., 1990; Katz et al., 1990), "single-strand gap filling and ligation" steps are needed before the retroviral/retrotransposon DNA can be incorporated stably. Despite the fact that the Ku-associated DNA repair apparatus is not known to function in single-strand gap-filling and ligation reactions, it is nevertheless demonstrated below that it is indeed required for the efficient integration of the yeast Ty1 and Ty5 retrotransposons and also effects the integration of retroviral cDNA into mammalian cells.

These surprising findings provide indication that the Ku-associated DNA repair apparatus plays a ubiquitous role in retrotransposon integration processes, and open up new opportunities for anti-retroviral action, as discussed.

According to one aspect of the present invention, there is provided a method of inhibiting retrovirus and/or retrotransposon activity by means of a substance identified as an inhibitor of Ku-associated DNA repair. Methods of treatment of the human or animal body by way of therapy may be excluded.

However, a further aspect of the present invention provides the use of a substance identified as an inhibitor of Ku-associated DNA repair in the manufacture of a medicament for inhibiting retrovirus and/or retrotransposon activity.

Another aspect of the present invention provides a substance identified as an inhibitor of Ku-associated DNA repair for use in inhibiting retrovirus and/or retrotransposon activity.

A further aspect of the present invention provides the use of a substance identified as an inhibitor of Ku-associated DNA repair in inhibiting retrovirus and/or retrotransposon activity.

The substance may be provided in a composition which includes at least one other component, for instance a pharmaceutically acceptable excipient, as discussed further below.

The substance may be provided in vivo to cells in a human or animal body, by way of therapy (which may include prophylaxis), or in planta, ex vivo or in vitro. This too is discussed further elsewhere herein.

Integration of a retrovirus and/or retrotransposon into the genome of a cell may be inhibited by treatment of the cell with a substance which is an inhibitor of Ku-associated DNA repair. Examples of such substances include wortmannin and LY294002 (Hartley et al., 1995).

Inhibition of Ku-associated DNA repair may be achieved in any of numerous different ways, without limitation to the nature and scope of the present invention.

In certain embodiments of the present invention, Ku itself is targeted for inhibition, that is to say that Ku's involvement in Ku-associated DNA repair is inhibited in order to inhibit Ku-associated DNA repair. Ku is only functional as a heterodimer (of subunits Ku70 and Ku80). One way, therefore, of inhibiting Ku activity is to inhibit interaction between the two subunits. Another way is to use a substance that inhibits interaction of Ku with DNA or another component of the Ku-associated DNA repair pathway. Otherwise, Ku itself need not be targeted and the function one or more other components of the Ku-associated DNA repair pathway may be inhibited (discussed further below). Of course, a substance may inhibit activity of a component of the pathway such as Ku not (or not solely) by inhibiting physical interaction between the component and another but by binding at an active site or by binding in a way that has a steric effect on the conformation of an active site and thus activity of the component. Precisely how the activity or function of a component of the pathway is inhibited need not be relevant to practising the present invention.

The sequences of various components of the Ku-associated DNA repair pathway in humans and yeast are available from the GenBank database, under the following accession numbers: human Ku70—J04611; human Ku80—M30938; S. cerevisiae Ku70—X70379; S. cerevisiae Ku80—Z49702; human ligase IV—X83441; S. cerevisiae ligase IV—YOR005c on the right arm of S. cerevisiae chromosome XV, accession number Z74913; human Rad50—U63139; S. cerevisiae Rad50p—X14814; human Mre11—U37359; S. cerevisiae Mre11—D11463; human XRCC4—U40622 (334 amino acid residue open reading frame); S. cerevisiae Xrs2p—L22856.

The activity or function of a component of the Ku-associated DNA repair pathway (such as Ku) may be inhibited, as noted, by means of a substance that interacts in some way with the component. An alternative employs regulation at the nucleic acid level to inhibit activity or function by down-regulating production of the component.

For instance, under-expression of a gene may be achieved using anti-sense technology. The use of anti-sense genes or partial gene sequences to down-regulate gene expression is now well-established.

Antisense oligonucleotides may be designed to hybridise to the complementary sequence of nucleic acid, pre-mRNA or mature mRNA, interfering with the production of a component of the Ku-associated DNA repair pathway, such as Ku, or a subunit thereof, encoded by a given DNA sequence, so that its expression is reduced or completely or substantially completely prevented. In addition to targeting coding sequence, antisense techniques may be used to target control sequences of a gene, e.g. in the 5' flanking sequence, whereby the antisense oligonucleotides can interfere with expression control sequences. The construction of antisense sequences and their use is described for example in Peyman and Ulman, Chemical Reviews, 90:543–584, (1990) and Crooke, Ann. Rev. Pharmacol. Toxicol., 32:329–376, (1992).

Oligonucleotides may be generated in vitro or ex vivo for administration or anti-sense RNA may be generated in vivo within cells in which down-regulation is desired.

Thus, double-stranded DNA may be placed under the control of a promoter in a "reverse orientation" such that transcription of the anti-sense strand of the DNA yields RNA which is complementary to normal mRNA transcribed from the sense strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works.

The complete sequence corresponding to the coding sequence in reverse orientation need not be used. For example fragments of sufficient length may be used. It is a routine matter for the person skilled in the art to screen fragments of various sizes and from various parts of the coding or flanking sequences of a gene to optimise the level of anti-sense inhibition. It may be advantageous to include the initiating methionine ATG codon, and perhaps one or more nucleotides upstream of the initiating codon. A suitable fragment may have about 14–23 nucleotides, e.g. about 15, 16 or 17.

Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Ausubel et al. eds., John Wiley & Sons, 1992, and *Molecular Cloning: a Laboratory Manual*: 2nd edition, Sambrook et al., 1989, Cold Spring Harbor Laboratory Press.

Another possibility is that nucleic acid is used which on transcription produces a ribozyme, able to cut nucleic acid at a specific site—thus also useful in influencing gene expression. Background references for ribozymes include Kashani-Sabet and Scanlon, 1995, *Cancer Gene Therapy*, 2(3): 213–223, and Mercola and Cohen, 1995, *Cancer Gene Therapy*, 2(1), 47–59.

It is well known that pharmaceutical research leading to the identification of a new drug may involve the screening of very large numbers of candidate substances, both before and even after a lead compound has been found. This is one factor which can make pharmaceutical research very expensive and time-consuming. Means for assisting in the screening process can have considerable commercial importance and utility. Such means for screening for substances potentially useful in inhibiting retroviral and/or retrotransposon activity is provided according to the present invention. Substances identified as modulators of Ku-associated DNA repair represent an advance in the fight against retroviral diseases (for instance), since they provide basis for design and investigation of therapeutics for in vivo use.

A method of screening for a substance which inhibits retrovirus and/or retrotransposon activity may include contacting one or more test substances with one or more components of the Ku-associated DNA repair pathway of an organism of interest in a suitable reaction medium, and testing for substance/component interaction, e.g. by assessing activity of the Ku-associated DNA repair pathway or component thereof and comparing that activity with the activity in comparable reaction medium untreated with the test substance or substances. A difference in activity between the treated and untreated samples is indicative of a modulating effect of the relevant test substance or substances. It may be sufficient, at least as a preliminary, to assess mere physical interaction between test substance and pathway component or subunit thereof in test samples, rather than actual biochemical activity.

In further aspects the present invention relates to the screening of candidate substances for potential as inhibitors of retrovirus and/or retrotransposon activity. More particularly, it provides a method by which test substances can be screened for their ability to affect Ku-associated DNA repair. Test substances may be screened for inhibition or activation of the pathway, though clearly inhibitors of the pathway are of primary interest.

According to a further aspect of the present invention there is provided a method of screening for a substance which is an inhibitor of retrovirus and/or retrotransposon activity, particularly nucleic acid integration or transposition of retrovirus and/or retrotransposon, which includes:

provided a Ku-associated DNA repair pathway;

exposing the pathway to a test substance under conditions which would normally lead to the activation of the Ku-associated DNA repair pathway; and looking for an end-point indicative of activation of the Ku-associated DNA repair pathway;

whereby inhibition of that end-point indicates inhibition of the Ku-associated DNA repair pathway by the test substance.

The pathway may be provided in a cell to be exposed to the test substance, or the assay may be performed on a in vitro Ku-associated DNA repair system that measures the accuracy and efficiency of joining together DNA strand breaks that have been created by treating intact DNA with restriction endonucleases, chemicals, or radiation.

Activation of the Ku-associated DNA repair pathway may be caused by DNA double-strand breaks (DSBs), single strand gaps in the DNA double helix and by other disruptions to the DNA double-helix. These structures exist at the ends of retroviral and retrotransposon DNA and occur as intermediates in the retroviral integration and retrotransposition process. To assay for Ku-associated repair, retrovirus or retroviral DNA, intermediates in retroviral integration or retrotransposon integration, or synthetic preparations of DNA that mimic any of these may be provided. The activation of the Ku-associated DNA repair pathway leads to the protection of DNA from excessive degradation and results in perturbations in the DNA double-helix via the ligation of DNA DSBs or single-strand breaks.

The end-point of the screen may be therefore the repair of such perturbations. That a substance is inhibitory of the Ku-associated DNA repair pathway may be verified by hypersensitivity of mammalian cells to ionising radiation (e.g. Jackson and Jeggo, and refs therein) or by rejoining of double-strand breaks (e.g. in a plasmid) in vivo (Boulton and Jackson, 1996a, 1996b). Biochemical methods, such as PCR or nucleic acid hybridisation/detection methods, may be used, e.g. to detect the chemical structure of integration products. Retroviral integration and/or retrotransposition may be scored for example by detection using standard genetic, biochemical or histological techniques.

It should be noted that in assaying for ability of a test substance to affect a Ku-associated DNA repair pathway, the end-point chosen to be determined in the assay need not be the actual end-point of the DNA repair pathway (the repair of DNA), but may be the activity which a component of the pathway exhibits in the pathway. Thus, for example, substances may be screened for ability to affect DNA-PK phosphorylation of other components of the pathway, such as XRCC4.

Of course, as noted elsewhere, reference to a component of a Ku-associated DNA repair pathway may be taken to refer to a derivative, variant or analogue of the relevant component which has the requisite, assayable property or activity (e.g. ability to bind another component in the pathway).

Given the teaching provided herein of the ability to inhibit retroviral and/or retrotransposon activity by manipulating the Ku-associated DNA repair pathway, those of ordinary skill in the art may design design assays for anti-retroviral agents by employing proteins or fragments thereof which are homologous with a component of the Ku-associated DNA repair pathway in the expectation that substances which affect the activity of the homologue will be able to affect the activity of the component.

Prior to, as well as or instead of being screened for ability actually to affect Ku-associated DNA repair activity, test substances may be screened for ability to interact with a component of the pathway (such as Ku or one or both of the subunits thereof) e.g. in a yeast two-hybrid system (which requires that both the polypeptide component and the test substance can be expressed in yeast from encoding nucleic acid). This may for example be used as a coarse screen prior to testing a substance for actual ability to modulate activity.

Thus, in a further aspect, the present invention provides a method of screening for a substance which is an inhibitor of retrovirus and/or retrotransposon activity, particularly nucleic acid integration of retrovirus and/or retrotransposon, which includes:

providing a component of a Ku-associated DNA repair pathway;

exposing the component to a test substance;

determining interaction between the component and the test substance.

A yeast two-hybrid system (e.g Evan et al. *Mol. Cell. Biol.* 5, 3610–3616 (1985); Fields & Song *Nature* 340, 245–246 (1989)) may be used to identify substances that interact with a Ku-associated DNA repair pathway component or subunit thereof. This system often utilises a yeast containing a GAL4 responsive promoter linked to β-galactosidase gene and to a gene (HIS3) that allows the yeast to grow in the absence of the amino acid histidine and to grow in the presence of the toxic compound 3-aminotriazole. The pathway component or subunit may be cloned into a yeast vector that will express the protein as a fusion with the DNA binding domain of GAL4. The yeast may then be transformed with DNA libraries designed to express test polypeptides or peptides as GAL4 activator fusions. Yeast that have a blue colour on indicator plates (due to activation of β-galactosidase) and will grow in the absence of histidine (and the presence of 3-aminotriazole) may be selected and the library plasmid isolated. The library plasmid may encode a substance that can interact with the Ku-associated.DNA repair pathway component or subunit thereof.

A variation on this may be used to screen for substances able to disrupt interaction between two components of the Ku-associated DNA repair pathway, or the subunits of a such a component (e.g. the Ku70 and Ku80 subunits of Ku—Ku is only functional as a heterodimer). For instance, the two components or subunits may be expressed in a yeast two-hybrid system (e.g. one as a GAL4 DNA binding domain fusion, the other as a GAL4 activator fusion) which is treated with test substances. The absence of the end-point which normally indicates interaction between the components or subunits (e.g. the absence of a blue colour in the exemplary system outlined above) when a test substance is applied indicates that that substance disrupts interaction between the two components or subunits, and may therefore inhibit Ku-associated DNA repair, indicative of potential as an inhibitor of retrovirus and/or retrotransposon activity.

For potential therapeutic purposes the Ku-associated DNA repair pathway or one or more components (or subunits) thereof used in the assay may be human, or mammalian or bird bearing in mind veterinary applications. However, given the ease of manipulation of yeast, and the good conservation between Ku-associated DNA repair components in different eukaryotes, an assay according to the present invention may involve applying test substances to a yeast system with the expectation that similar results will be obtained using the substances in mammalian, e.g. human, systems. In other words, a substance identified as being able to inhibit Ku-associated DNA repair in yeast is likely to be able to inhibt Ku-associated DNA repair in other eukaryotes. A further approach, as discussed, is to use yeast cells expressing one or more components (e.g. Ku) or subunits (e.g. Ku70/Ku80) of the Ku-associated DNA repair pathway of another eukaryote, e.g. human. A plant Ku-associated repair pathway or one or more components thereof may be employed in an assay according to the present invention, to test for substance useful in inhibiting retroviral and/or retrotransposon activity in the plant or plants generally.

Following identification of a substance which modulates or affects Ku-associated DNA repair and/or interaction between components of the pathway or subunits thereof, the substance may be investigated further, in particular for its ability to inhibit retroviral and/or retrotransposon activity. Furthermore, it may be manufactured and/or used in preparation, i.e. manufacture or formulation, of a composition such as a medicament, pharmaceutical composition or drug. These may be administered to individuals.

Thus, the present invention extends in various aspects not only to a substance identified as inhibiting retroviral and/or retrotransposon activity in accordance with what is disclosed herein, but also a pharmaceutical composition, medicament, drug or other composition comprising such a substance, a method comprising administration of such a composition to a patient, e.g. for .treatment (which may include preventative treatment) of a retroviral disorder, use of such a substance in manufacture of a composition for administration, e.g. for treatment of a retroviral disorder, and a method of making a composition comprising admixing such a substance with a pharmaceutically acceptable excipient, vehicle or carrier, and optionally other ingredients.

A substance that tests positive in an assay according to the present invention or is otherwise found to inhibit retroviral and/or retrotransposon activity by inhibition of Ku-associated DNA repair may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, eg by substituting each residue in turn. Alanine scans of peptide are commonly used to refine such peptide motifs. These parts or residues constituting the active region of the compound are known as its "pharmacophore".

Once the pharmacophore has been found, its structure is modelled to according its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. Alternatively, where the mimetic is peptide based, further stability can be achieved by cyclising the peptide, increasing its rigidity. The mimetic or mimetics found by this approach can then be screened to see whether they have the target property, or to what extent they exhibit it. Further optimisation or modification can then be carried out to arrive at one or more final mimetics for in vivo or clinical testing.

A substance for inhibiting retrovirus and/or retrotransposon activity in accordance with any aspect of the present invention may be formulated in a composition. A composition may include, in addition to said substance, a pharmaceutically acceptable excipient, carrier, buffer, stabiliser or one or more other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at a particular site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Whether it is a polypeptide, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980.

Targeting therapies may be used to deliver the active agent more specifically to certain types of cell, by the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells. The vector may be targeted to the specific cells to be treated, or it may contain regulatory elements which are switched on more or less selectively by the target cells.

The agent may be administered in a precursor form, for conversion to the active form by an activating agent produced in, or targeted to, the cells to be treated.

A composition may be administered alone or in combination with other treatments, either simultaneously or sequentially dependent upon the condition to be treated.

The experimental basis for the invention and illustrative embodiments of the invention will now be described in more detail, with reference to the accompanying drawings. All publications mentioned in the text are incorporated herein by reference.

FIG. 1 shows that inactivation of YKU70 or YKU80 leads to reduced frequencies of Ty1 transposition.

FIG. 2 shows that transposition by Ty5 is debilitated by mutations in YKU70, but not RAD52. Relative transposition frequencies are shown for wild-type, yku70, rad52 and yku70/rad52 cells which were in each case transformed with a plasmid (pSZ152, Zou et al. 1996) bearing the Ty5 retrotransposon and containing the same HIS3-artificial intron construct as pGTy1H3mHIS3AI (Curcio and Garfinkel, 1991). Frequencies are given relative to wild-type, which had a mean Ty5 transposition frequency of $3.2 \times 10^{-4}$.

FIG. 3 shows that Ku does not appear to affect the generation of Ty1 VLPs. The graph shows reverse transcriptase activity ($^{32}$P incorporated; cpm) for sucrose gradient fractions. Triangles plot activity for cells which are yku70+Ty1, shown to be similar to cells which are wild-type+Ty1 (ovals). Activity for wild-type controls (no Ty1) is plotted with squares.

FIG. 5 shows results of analysis of 3'–5' degradation of Ty1 cDNA. Ty1 VLP DNA isolated from wild-type or yku70 yeast cells was incubated with Klenow (lacking exonuclease activity) and radioactive dNTPs. Klenow-mediated (5'–3') nucleotide incorporation was measured by scintillation counting and the results are shown as $^{32}$P counts incorporated relative to wild-type.

FIG. 6 shows that degradation activity for VLP-associated DNA is lower in VLPs isolated from wild-type strains than from yku70 strains.

EXPERIMENTAL WORK

Yeast Cells

To test the potential involvement of Ku in retrotransposition, the yeast *S. cerevisiae* was used as a model system. Notably, recent studies have revealed that the Ku-associated DNA DSB repair system is highly conserved between yeast and humans (Boulton and Jackson, 1996a; Boulton and Jackson, 1996b and references therein). Furthermore, it is clear that the yeast retrotransposons Ty1 and Ty5 transpose through mechanisms that are highly related to those of retrotransposons and retroviruses in other organisms, including humans (Boeke et al., 1985; Garfinkel, 1985; Boeke and Sandmeyer, 1991).

To assess the efficiency of retrotransposition, the galactose-inducible Ty1 transposition system (Curcio and Garfinkel 1991) was initially utilised. In this system, a his3 mutant derivative of the yeast strain under investigation is generated such that it contains an episomal replicating plasmid that directs the expression of Ty1 RNA from a galactose-inducible promoter. Importantly, the Ty1 element contains within it the *S. cerevisiae* HIS3 gene that is interrupted by an intron in reverse (anti-sense) orientation. Thus, the yeast strain is phenotypically his– and cannot grow in the absence of histidine in the growth medium. However, since the intron is in the sense orientation with respect to the Ty1 retroelement, it can become removed by splicing of the Ty1 RNA when this is produced in the presence of galactose. If this spliced RNA subsequently becomes reverse transcribed and integrated by the Ty1 integrase into the yeast genome, the now intron-less yeast HIS3 gene can now be expressed, and the resulting yeast strain is converted to a HIS+ phenotype. Hence, this assay system allows the efficiency of retrotransposition to be determined by quantifying the ability of the yeast strain being tested to generate HIS+ colonies after galactose induction.

Transposition assays were performed as follows. Yeast strains were transformed with pGTy1-H3mHIS3AI (Curcio and Garfinkel, 1991) or pSZ152 and plated to select for the URA3 gene on this plasmid (on synthetic media without uracil, SC-ura). These plasmids contain a galactose-inducible Ty1 or Ty5 element respectively, under control of the galactose inducible GAL1-10 promoter, and a HIS3 gene with an artificial intron in the reverse orientation. Expression of the HIS3 gene is dependent on transcription and transposition of the Ty1 element (Curcio and Garfinkel, 1991). Individual colonies were picked and grown in galactose-containing media overnight at 30° C. The optical density of cultures was measured at 595 nm to determine cell density, and plating on synthetic complete medium lacking uracil was used to determine cell viability. Cells were also plated onto synthetic complete medium containing glucose and lacking histidine, and the number of colonies arising divided by the total cell count was obtained as a measure of the Ty1 transposition frequency in each strain tested. Frequencies are shown (in FIGS. 1A, 1B, 1C and 1D) relative to wild type, which had a mean transposition frequency of $1.5 \times 10^{-4}$. All assays were conducted a minimum of three times.

Yku70p is Required For Effective Transposition By Ty1

Figure 1A:
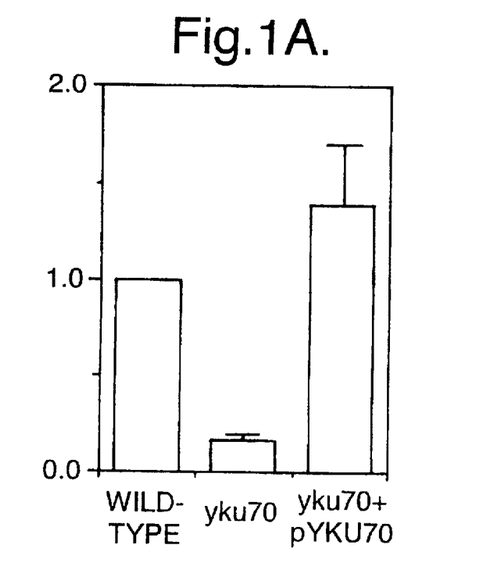
FIG. 1A shows transposition frequencies of Ty1 in wild-type *Saccharomyces cerevisiae* strain W303-1A (Wild-type), in a W303-1A derived yku70 mutant yeast strain (yku70), and in the yku70 mutant strain containing an episomal plasmid that expresses the wild-type YKU70 gene (yku70/pYKU70), calculated relative to wild-type yeast (for details of yeast strains and YKU70 plasmid, see Boulton and Jackson 1996).

As shown in FIG. 1A, a yeast strain deficient in the gene for yeast Ku70 (YKU70) gives rates of retrotransposition that are 5 to 10-fold lower (i.e. decrease of >80%) than that of the control yeast strain. That this defect is due to inactivation of YKU70 is revealed by the fact that the defect is observed with several independently-derived yku70 mutant strains (data not shown). Moreover, the transposition defect is fully complemented when the yku70 mutant strain contains an episomal plasmid containing the YKU70 gene (FIG. 1A). This demonstrates that Yku70p plays an important role in Ty retrotransposition.

Figure 1B:
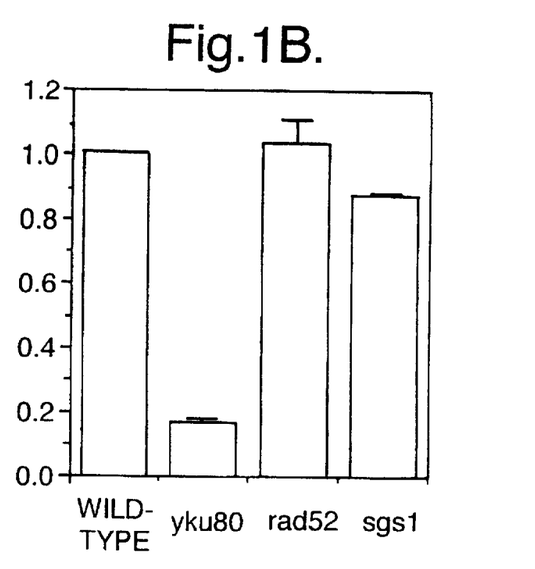
FIG. 1B shows that inactivation of YKU80 but not RAD52 or SGS1 leads to reduced frequencies of Ty1 transposition. The wild-type strain W303-1A (Wild-type) or W303-1A derived strains deficient in YKU80 (yku80), RAD52 (rad52) or SGS1 (sgs1) were tested for their ability to support Ty1 retrotransposition. Transposition frequencies are shown normalised to the wild-type strain.

Yku80p is Also Required For Effective Transposition By Ty1 But Components of Other DNA Repair Pathways Tested Are Not To see whether the transposition defect observed above is specific to mutations in YKU70, yeasts defective in other DNA repair components were tested for Ty1 transposition. As shown in FIG. 1B, inactivation of YKU80, the gene for yeast Ku80, also leads to a dramatic decrease in retrotransposition frequencies. By contrast, inactivation of the DNA repair gene RAD52 or the gene for the putative DNA repair factor Sgs1p do not have a significant effect on the frequency of retrotransposition.

It is therefore concluded that Ty1 retrotransposition is affected negatively by mutations in the genes for Yku70p and Yku80p but not by mutations in other DNA repair pathways analysed.

Figure 1C:
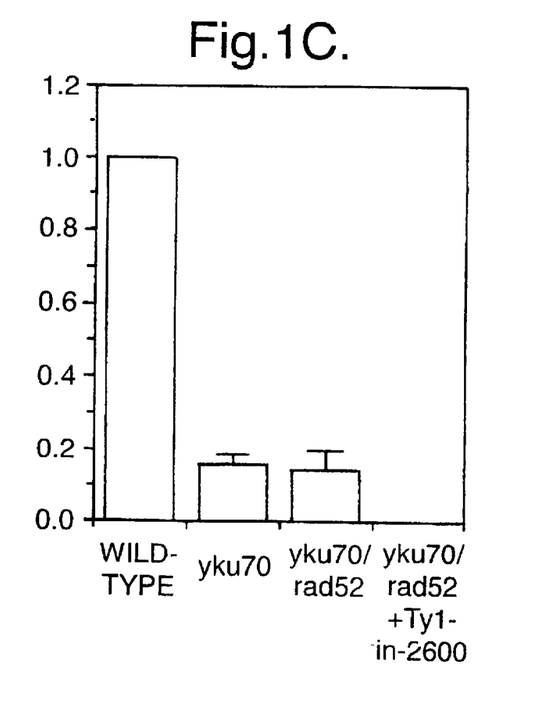
FIG. 1C shows Ty1 transposition frequencies in yku70, yku70/rad52, and yku70/rad 52 with Ty1-in2600 relative to wild-type.
Figure 1D:
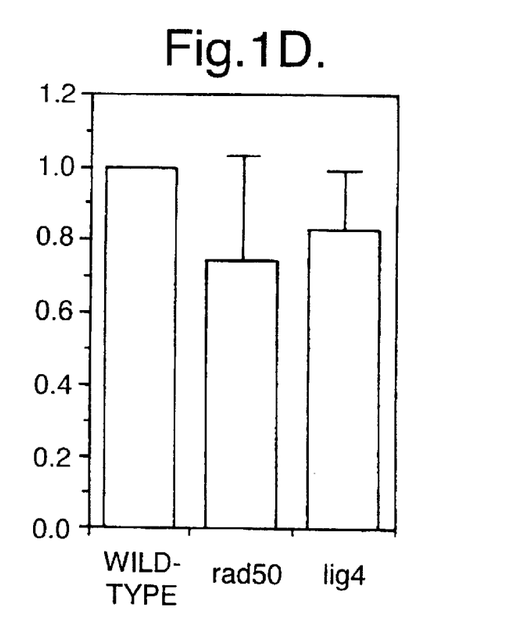
FIG. 1D shows Ty1 transposition frequencies in rad50 and lig4 mutant strains relative to wild-type.

Residual Integration in Yku70 Strains is Not Mediated Via Homologous Recombination Previous work has shown that Ty1 DNA integrates at low levels into the yeast genome via homologous recombination (Melamed, et al. 1992; Sharon, et al. 1994). However, retrotransposition in yku70 mutant strains is not reduced further upon inactivation of RAD52 (FIG. 1C), indicating that residual integration in yku70 strains is not mediated via homologous recombination. It has also been shown that the His$^+$ phenotype in the Ty1 retrotransposition assay can be achieved by a mechanism that is independent of both integrase and homologous recombination, and that many His$^+$ colonies resulting from this mechanism carry HIS3 on the plasmid (Sharon, et al. 1994). However, when residual His$^+$ cells arising in yku70 mutant yeast were induced to lose the Ty1 bearing plasmid by selection on fluoro-orotic acid, all surviving colonies were still His$^+$ (120/120 for wild-type, 118/118 for yku70), revealing that HIS3 was inserted into the genome. In addition, retrotransposition assays were performed using an integrase-deficient Ty1 element [in-2600; (Sharon, et al. 1994)]. Notably, in yku70 mutant strains, the loss of both RAD52 and a functional integrase results in abrogation of retrotransposition rates in the assay used (FIG. 1C). Therefore, the vast majority of residual His$^+$ cells generated in yku70 strains result from integrase-mediated events.

Ku is Required For Efficient Transposition By Other Types of Retrotransposon

To see whether the effect of Ku on retrotransposition is specific to Ty1, or whether it extends to other retrotransposable elements, transposition of the divergent retrotransposon Ty5 was also assessed. Yeast strains were transformed with a plasmid containing the Ty5 element under the control of the GAL1 promoter, and containing the same HIS3 artificial intron construct as pGTy1-H3mHIS3AI (plasmid psz152 Zou et al. 1996) and assays were performed as described above with reference to FIG. 1.

Figure 2:
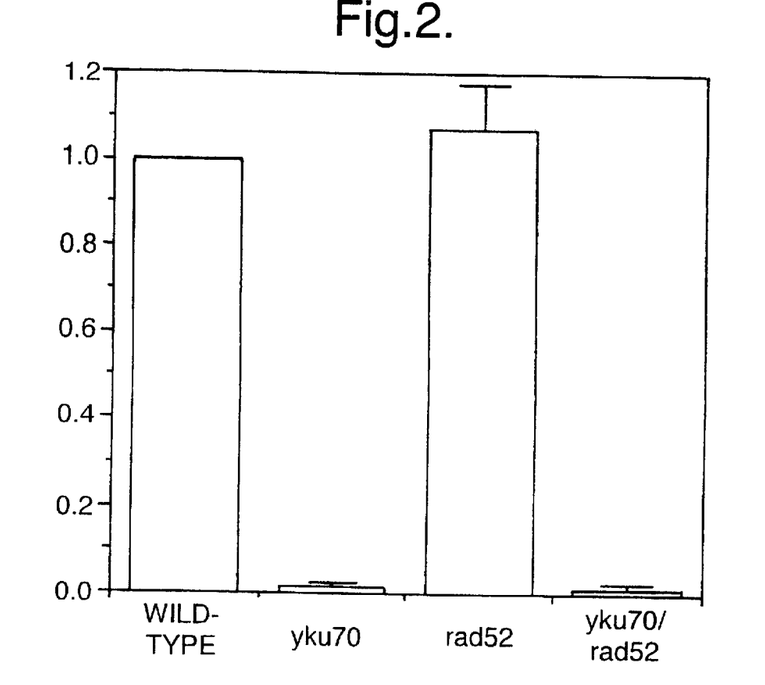

Strikingly, the efficiency of Ty5 transposition is reduced about 100-fold when yeast strains possess mutations in either YKU70 or YKU80 (FIG. 2). By contrast, inactivation of the DNA repair gene RAD52 has no significant effect on Ty5 transposition rates, in either a wild-type or yku70 mutant background. Other studies indicate that mutation in YKU80 or mutation in SIR2, SIR3 or SIR4 depress Ty5 retrotransposition substantially, and that YKU70 or YKU80 also impair transposition by the yeast retrotransposon Ty3 (data not shown). Taken together, these data reveal that defects in Ku lead to dramatically reduced transposition frequencies of three divergent retrotransposons. This therefore reveals that Ku affects a fundamental aspect of the retrotransposon life cycle.

Yeast Ku Does Not Affect the Formation of Functional Virus-Like Particles

There are several stages in the Ty life cycle at which Ku could function. First, Ku could affect the synthesis of the virus-like particles (VLPS) by affecting the synthesis of the Ty RNA, the sy nthesis of other viral components, or the reverse transcription of the RNA and its assembly into an infective VLP. Second, Ku could affect the stability of the VLP or the DNA that it contains. Third, Ku could affect the ability of the VLP to integrate into target DNA. Fourth, Ku could be involved in DNA repair steps that occur subsequent to the initial integrase-mediated DNA strand cleavage and transfer reactions.

Figure 3:
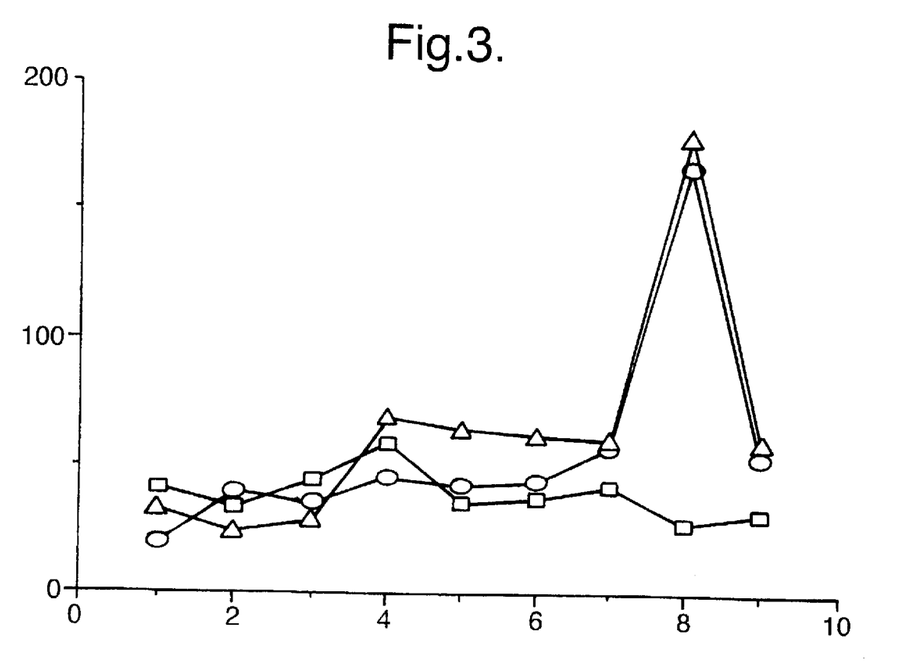

To investigate the m e chanism by which Ku affects retrotransposition for Ty1, Ty1 VLPs from actively transposing cells were isolated and analysed. Notably, VLPs isolated from wild-type and yku70 cells had similar RT activity profiles across a sucrose gradient used in their isolation (FIG. 3; wild-type cells without the Ty1 element were also analysed to provide background RT activity levels). Since Ku binds to DNA ends, we reasoned that Ku might be bound to the linear Ty1 cDNA in the VLPs. To determine whether Ku is associated with the VLPs, Western blot analyses were performed on sucrose gradient fractions using a polyclonal anti-Yku70p antibody. Yku70p was thus detected in fractions 1 and 2 of extract from wild-type cells either lacking or containing actively transposing Ty1. Most significantly, however, yku70p was also detected in fraction 8 of wild-type Ty-containing extracts that contains peak RT activity, but was not detected in the equivalent fraction derived from cells lacking Ty1. The presence of Yku70p in fractions containing peak RT levels was found consistently in three independent VLP preparations. Furthermore, Western blot analysis of similar preparations from cells containing actively transposing Ty5 also showed an association of Yku70p with peak RT levels. Together, these data suggest strongly that Yku70p associates with Ty VLPS.

Whole cell extracts prepared from the indicated yeast strains were fractioned over a sucrose gradient and assayed for RT activity. Isolation of VLPs was adapted from Eichinger and Boeke (1988). Briefly, 5 ml of overnight yeast culture containing pGTyH1mHIS3AI (grown in SC-ura containing glucose) was pelleted, washed with water, and used to inoculate 50 ml of SC-ura containing galactose. Wild-type cells containing no plasmid were grown in SC (containing either glucose or galactose, as above) and processed in parallel. After growing for 24 hours at 22° C., cells were harvested, washed with water, and lysed by glass bead disruption in the presence of 1 ml Buffer B/Mg (10 mM HEPES, pH 7.6, 15 mM KCl, 3 mM DTT, 0.01 mg/ml aprotinin, 5 mM $MgCl_2$). Lysate was centrifuged at 12,000 g, and the supernatant loaded onto a sucrose gradient (1 ml of 70% sucrose in Buffer B without $MgCl_2$ and with 10 mM EDTA, 1 ml of 30%, and 4 ml of 20%). Gradients were centrifuged in a Beckman SW-40 rotor at 4° C. for 4 hours. Fractions (0.75 ml) were collected and tested for RT activity. Positive fractions were pelleted at 50,000 g overnight at 4° C., resuspended in 10 µl of Buffer B/Mg, and stored at 4° C.

Western blot analysis was performed on the sucrose gradient fractions with anti-Yku70p antibody. Nuclear extracts from either wild-type or yku70 strains were also analysed. Yeast extracts were harvested and fractionated over sucrose gradients as above. All fractions were pelleted at 100,000 g overnight at 4° C. and resuspended in 10 µl Buffer B/$Mg^{2+}$. Five µl of each fraction was analysed by 8% SDS PAGE and transferred to a nylon membrane. The membrane was incubated with rabbit polyclonal anti-Yku70p antiserum and visualised with horseradish peroxidase-coupled anti-rabbit IgG and enhanced chemiluminescence (Amersham). Yku70p is a ~67 kDa protein recognised in wild-type extracts but not seen in yku70 extracts.

Figure 4:
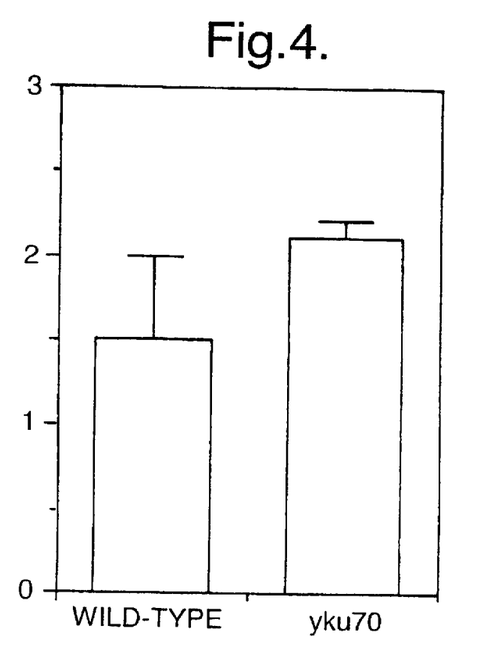
FIG. 4 shows that VLPs isolated from Yku70p-deficient yeasts are competent for Ty1 integrase-mediated transposition in vitro. Transposition frequency ($\times 10^{-3}$) is plotted for wild-type and yku70 cells.

To see whether the VLPs isolated from Ku positive and Ku negative yeast cells differ functionally, the abilities of the two VLP preparations to integrate into a plasmid DNA molecule in vitro were compared. As shown in FIG. 4, VLPs isolated from Ku deficient cells are no less active in mediating cDNA integration than the VLPs isolated from Ku positive yeasts.

In vitro transposition was assayed using VLPs that had been purified from a wild-type or a yku70 mutant (yku70) yeast strain, as described above with reference to FIG. 3. Reactions contained 3 ml VLPs or Buffer B/$Mg^{2+}$(negative control), 10 mM Tris pH 8.0, 15 mM $MgCl_2$, 1 mM DTT, 5% polyethylene glycol, and 1 mg of supercoiled plasmid DNA (pRS416; Stratagene). Reactions were incubated for 30 min at 25° C., and stopped by the addition of proteinase K to 0.5 mg/ml and SDS to 1.4% followed by a further incubation at 25° C. for 3h. Next, the DNA was extracted with phenol/chloroform, precipitated with ethanol, washed with 70% ethanol, resuspended in 10 mM Tris pH 8.0, and transformed into XL-1 cells (Stratagene). Colony hybridization was performed using a random-primed probe corresponding to the HIS3 gene. Positive colonies were counted relative to total colonies to give the average transposition frequency. Positive colonies were picked to ensure they contained the Ty1 element; as expected, reactions containing no VLPs yielded no positively hybridising colonies.

Taken together, these data provide indication that Ku does not affect the synthesis, stability or inherent catalytic activity of Ty element VLPs.

Identifying the Step of the Retrotransposon/Retrovirus Life Cycle That is Affected By the Ku-Associated DNA Repair Apparatus There are several possibilities for how Ku potentiates retrotransposition and all are testable.

(1) It is possible that Ku binds to the retrotransposon or retrovirus cDNA in the VLPs or the retrovirus particle (RP) as a way to increase particle stability or rate of assembly. This possibility may be tested by using antibodies against Ku subunits in immunoprecipitation and Western blotting studies with VLPs and virus particles.

(2) Ku could protect the ends of the cDNA from nucleases or other DNA modifying enzymes. This could occur when the cDNA is in the VLP or (retroviral particle) RP and may be tested simply by determining the precise sequence of the Ty cDNA ends by cloning and sequencing of the cDNA ends derived from VLPs or RPs, or assays such as primer extension, ribonuclease or S1 nuclease mapping procedures (Ausubel et al., 1991).

(3) Ku may prevent "auto-integration" processes leading to a destruction of the VLP or RP cDNA by one molecule integrating into another. Auto-integration events have been demonstrated previously (Lee and Craigie, 1994 and references therein), so it will be easily possible to test whether Ku is able to affect this process. Such assays will utilise VLPs or infective RPs in in vitro transposition reactions in the presence or absence of purified yeast Ku (Feldmann and Winnacker, 1993) or human Ku (Dvir et al., 1993; Hartley et al., 1995).

(4) Ku could function in vivo to tether the integration machinery to sites on the chromosomal DNA (this type of process has been shown to affect the efficiency of transposition; Bushman, 1994). To test this, the ability of Ku to interact with VLPs or RPs can be assessed in vitro by standard biochemical assays or by protein affinity chromatography procedures (eg. tether Ku to an insoluble support and see whether this retains VLPs or RPs).

(5) Ku could affect the efficiency of integration or could drive the reaction to completion by preventing reverse reactions from taking place (reversal of integration can take place in vitro; for example, Chow et al. 1992). This may be tested by assessing the effect of adding purified yeast or mammalian Ku to in vitro retrotransposition reactions using purified integrase proteins or with VLPs or RPs (for example, Brown et al. 1987; Eichinger and Boeke, 1988; Fujiwara and Mizuuchi 1988; Fujiwara and Craigie 1989; Craigie et al. 1990; Bushman et al., 1990; Katz, et al., 1990; Bushman and Craigie 1991; Pryciak et al. 1992; Moore and Garfinkel 1994; and references therein). In addition, effects of Ku on integration reactions may be investigated by assaying the effects of extracts from Ku-containing or Ku-deficient mammalian or yeast cells to in vitro integration assays.

(6) Ku could be involved in the repair of the integrated products—integrase is capable of joining the viral cDNA to another DNA molecule but these products retain nicks and/or gaps and these must be processed before the DNA can be propagated (for example, Bushman et al., 1990; Craigie et al., 1990). It is possible that the Ku-associated DNA repair apparatus performs these functions. Such models may be tested by introducing the nick-containing intermediates of in vitro retrotransposon/retrovirus integration reactions into Ku positive or Ku negative yeast or human cells, then analysing their repair in vivo. This type of analysis may also be conducted with artificial substrates that mimic nicked integrase-generated retrovirus/retrotransposon integration intermediates. Another way to address this is to analyse the processing of natural or artificial nicked substrates in vitro using extracts of yeast or human cells that are proficient or deficient in components of the Ku-associated DNA repair system, or by using (part) purified components of the Ku-associated DNA repair system.

It is important to note that for performance of the present invention in various aspects it is not necessary to know how Ku is involved in the retrovirus/retrotransposon life cycle. It can simply be noted that it is so involved and that, as demonstrated herein, disruption of Ku function has an anti-retroviral/anti-retrotransposon effect.

Inhibition of Yeast Ku Activity Leads to Reduced Ty Transposition Frequencies

The loss of yeast Ku function affects Ty transposition rates (established above) provides indication that, Ty transposition frequencies will be reduced in Ku positive cells by inhibitors of Ku action.

One approach to demonstrate this principle involves introduction into YKU70/YKU80 strains of plasmid molecules that direct the expression of mutated derivatives of Yku70p or Yku80p (using the vectors such as those described previously; Boulton and Jackson, 1996a; Boulton and Jackson, 1996b). The Ku mutants studied may for example include N-terminal deletion mutants, C-terminal deletion mutants, and point mutants in regions of the protein that are conserved throughout evolution (e.g. Feldmann and Winnacker, 1993; Boulton and Jackson, 1996b). Since the subunits of Ku function as a heterodimer and work in association with various other proteins, various mutated Ku molecules able to interact with their partner or with other components of the system will form non-functional complexes. Such dominant negative mutations, when used in Ty transposition studies, provide indication that inhibition of Ku function can impair Ty retrotransposition.

Definition of the Regions of Yku70p and Yku80p That Function in Ty Integration

The regions of the two Ku subunits that function in Ty retrotransposition may be defined by assessing the abilities of mutated derivatives of YKU70 and YKU80 to complement the transposition deficiencies of yku70 and yku80 mutant strains, respectively (using vectors such as those described previously; Boulton and Jackson, 1996a; Boulton and Jackson, 1996b). The ability of the mutated Yku70p and Yku80p derivatives to complement the DNA repair, radiosensitivity and telomeric loss phenotypes of Ku-deficient yeasts may also be tested using standard procedures (Boulton and Jackson, 1996a; Boulton and Jackson, 1996b; Porter et al., 1996). Similar approaches may also be used to define important functional regions of mammalian Ku70 and Ku80 and define functional regions of other components of the Ku-associated DNA repair apparatus (see below).

The identification of regions that affect retrotransposition selectively, may lead to the development of drugs that interfere with retrotransposition but do not affect other Ku-dependent processes.

Effects of Other Components of the Ku-Associated DNA Repair Apparatus on Retrotransposition The results obtained with Ku, lead to an expectation that other proteins that function in Ku-associated processes will play a role in retrotransposon and retroviral integration. Unpublished data from the inventors' laboratory indicate that the products of the yeast genes RAD50, XRS2, and MRE11 function with Yku70p and Yku80p in DNA DSB rejoining. Thus, disruption of the MRE11, XRS2, or RAD50 genes results in defects in illegitimate end-joining as ascertained by plasmid repair assays and in radiosensitivity experiments such as those described previously (Boulton and Jackson, 1996a, 1996b). These defects are the same as those observed in strains disrupted for YKU70 or YKU80 (Boulton and Jackson, 1996a and 1996b). Furthermore, no additional defect in DNA repair is observed in double-mutant strains deficient in Ku plus any one of these other genes (MRE11, XRS2, RAD50). These data therefore indicate that MRE11, XRS2 and RAD50 function in the same DNA DSB repair pathway as Ku. Further results show that the yeast gene that we term LIG4 (Teo et al., 1997) is also part of the Ku-associated DNA repair apparatus. This corresponds to open reading frame YOR005c on the right arm of S. cerevisiae chromosome XV, accession number Z74913 of the yeast genome database, and encodes a protein with strong sequence similarity to mammalian ligase IV (Wei et al., 1995). Disruption of LIG4 results in defects in illegitimate end-joining as ascertained by plasmid repair assays and in radiosensitivity experiments and these defects are the same as those observed in strains disrupted for YKU80 (Boulton and Jackson, 1996a, 1996b). Furthermore, no additional defect in DNA repair is observed in double-mutant strains deficient in Ku plus LIG4, indicating that these genes function in the same pathway. The effect of mutating these genes on Ty retrotransposition frequencies may be tested using assays similar to those described for Ku.

For instance, FIG. 2D shows some decrease in retrotransposition rates in strains that have disruptions in either RAD50 or LIG4. These have been shown to work in the same pathway as Ku in repairing ds breaks in yeast (Milne et al., 1996; Tsukamoto et al., 1996; Teo et al., 1997; Shar et al., 1997; Wilson et al, 1997). The decreases were not as great as expected, suggesting that Ku might be facilitating retrotransposition in a manner distinct from its role in repairing DNA ds breaks. In further studies, disruption of SIR2, SIR3 or SIR4, which also function in the Ku-associated pathway of DNA DSB repair (Tsukamoto et al., 1997; Jackson, 1997) leads to decreased retrotransposition rates. Thus, inhibition of mammalian homologues of such factors (Baker et al., 1995) provides a further alternative for development of anti-retroviral agents.

Should a yeast homologue of the mammalian XRCC4 protein (Li et al., 1995) be identified, this will also be expected to be involved in Ty transposition because the mammalian factor functions as part of the Ku-associated DNA repair apparatus (and see below) and defects in mammalian XRCC4 negatively affect retrovirus integration (see below). If any other components of the yeast Ku-associated DNA repair apparatus are defined, these will also be tested for their role in retrotransposition. Should mutation of any of these genes lead to reduced retrotransposition, then these factors, and their homologues in other organisms, will be attractive targets for the development of novel anti-retroviral agents.

Steps to determine the site(s) of involvement of additional factors in retrotransposition and the development of strategies for drug screening etc. will be analogous to those described above and below for the Ku subunits.

Ku Protects Retroelement DNA From Cellular Nucleases

In light of the effect of Ku on retrotransposition, and since Ku binds to DNA ends, one possibility is that Ku enhances retrotransposition by binding to retrotransposon CDNA and protecting it from nuclease attack. Indeed, while reverse transcription of retroviral and Ty element RNA occurs inside viral particles or VLPs (Garfinkel et al. 1985; Zang, 1995; Mellor 1985), there is evidence that the DNA contained within these particles is susceptible to nucleases (Bowerman, 1989). To establish whether lack of Ku leads to degradation of retrotransposon cDNA, DNA was isolated from Ty1 VLP preparations derived from wild-type or yku70 cells, digested with SpeI and the resulting moecules incubated with Klenow and radioactive dNTPs. The SpeI products include a 287 bp fragment corresponding to the 3' end of the Ty1 element. If the ends were degraded significantly in the VLPs derived from yku70 cells, this band would be expected to run faster or appear smeared relative to the corresponding fragment from wild-type VLPS. However, no detectable differences were detected between the cDNAs products derived from wild-type and yku70 cells.

For Southern analysis of Ty1 cDNA, VLPs from wild-type or yku70 strains were normalised by RT activity and incubated at room temperature in Buffer B/$Mg^{2+}$ (10 mM HEPES, pH 7.6, 15 mM KCl, 3 mM DTT, 10 mg/ml aprotinin, 5 mM $MgCl_2$). DNA was isolated by phenol/chloroform extraction at various time points and electrophoresed on a 1% agarose gel. The gel was transferred and analysed by Southern blott-hybridisation followed by autoradiography.

Equal amounts of VLP preparations as determined by RT activity were used for analyses of Ty1 DNA. DNA was isolated by incubation with 50 ng/ml proteinase K, 12.5 mM EDTA, and 0.5% SDS at 25° C. for 2 hours followed by two phenol/chloroform extractions and ethanol precipitation. For Southern analysis, Ty1 DNA was analysed by 1 & agarose electrophoresis and transferred to GeneScreeen Plus (DuPont/NEN). The membrane was probed with the BamHI/HindIII fragment of pGTy1H3mHIS3AI that was labelled by nick translation (Promega).

Figure 5:
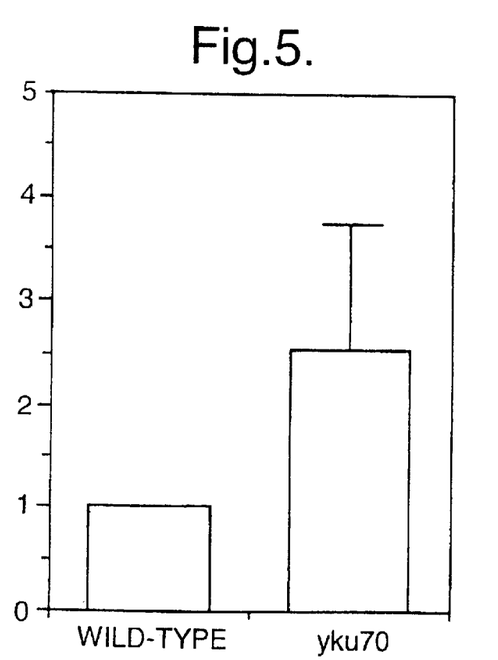

Although the above data revealed that no large-scale degradation of VLP DNA had occurred in the absence of Ku, small amounts of degradation would not have been detected. To detect low levels of degradation, VLP DNA was incubated with radioactive dNTPs and the Klenow fragment of *E. coli* DNA polymerase, then was analysed by scintillation counting. Since Klenow polymerises in a 5' to 3' direction, the amount of incorporation is a relection of DNA nicks or recessed 3' ends. Significantly, cDNA isolated from yku70 VLPs incorporated ~2-fold more radiolabel than CDNA from wild-type VLPs (FIG. 5). These data suggest that Ty1 cDNA accumulates increased levels of DNA nicks in the absence of Ku and/or displays 3' to 5' degradation of the cDNA ends. Since Ty1 integrase requires either blunt ends or an overhanging 3'-OH to catalyse strand exchange (Eichinger and Boeke, 1990), such 3' to 5' degradation could adversely affect retrotransposition efficiency.

Figure 6A:
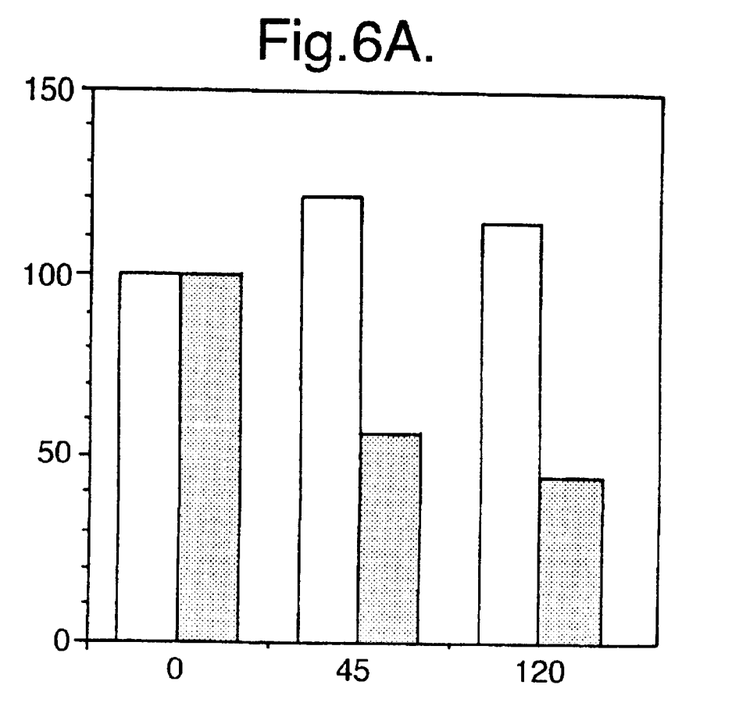
FIG. 6a shows quantitation of Ty1 cDNA isolated from wild-type or yku70 strains (% full-length Ty1 element) at various time points (minutes). VLPs, normalised by RT activity, were incubated at room temperature for the indicated lengths of time. For each time point the figure for wild-type cells is shown as the left block, with the figure for yku70 cells as the right block.
Figure 6B:
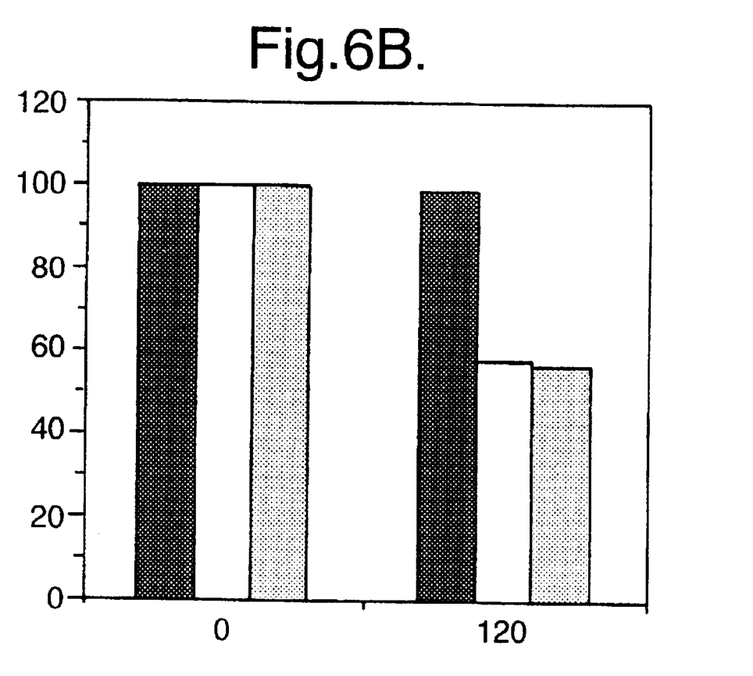
FIG. 6b shows that VLP preparations from wild-type and yku70 mutant strains have equivalent levels of intrinsic nuclease activity. Blunt-ended plasmid DNA was incubated with buffer alone (left block for each time point) or VLPs from either wild-type (middle block for each time point) or yku70 cells (right block for each time point). % full-length plasmid DNA is shown for each time point.

There is a nuclease activity that co-purifies with the VLPs over sucrose gradients (Braiterman and Boeke, 1994). VLP preparations derived from Ku positive and Ku negative yeast cells were incubated at room temperature for various lengths of time, then analysed the Ty1 DNA for degradation by Southern hybridisation analysis. Notably, these studies revealed that VLP-associated Ty1 DNA derived from yku70 cells degrades much more rapidly than that obtained from wild-type cells (FIG. 6a). By contrast, plasmid DNA degraded equally quickly when added to the two VLPs preparations (FIG. 6b). The lower rate of degradation in wild-type cells, therefore does not appear to be due to the absence of active nuclease in the VLP preparations derived from yku70 mutant cells. Instead, these data suggest strongly that the association of Ku with Ty1 VLPs protects Ty1 cDNA from nuclease attack. Blunt-ended plasmid DNA (pRS416; 2 μg) was incubated with buffer alone or VLPs from either wild-type or yku70 (the quantity of VLPs used in the reactions was normalised by RT activity). DNA was incubated for the time indicated, electrophoresed on a 1% agarose gel, visualised by staining with ethidium, and quantitated.

The above results indicate a role for Ku in retrotransposition, and suggest that it functions, at least in part, by binding to and protecting the retroelement DNA from cellular nucleases. In line with this model, Ku has been shown to function in the accurate repair of DNA double-strand breaks (DSBS) in yeast, and linear DNA repaired in the absence of Ku contains deletions (Mages et al., 1996; Boulton and Jackson, 1996a; Boulton and Jackson, 1996b; Milne et al., 1996; Siede et al., 1996; Tsukamoto et al., 1996). Since the association of Ku with DNA ends is highly stable, it is conceivable that Ku remains associated with the Ty1 cDNA during transport into the nucleus and functions in subsequent steps in the retrotransposition process. For example, as Ku binds to DNA ss gaps with comparable affinity to DNA ds ends (Paillard and Strauss, 1991; Falson et al., 1993), it might facilitate the repair of the single-stranded DNA gaps that arise as retrotransposition intermediates. Through binding to such structures and displacing integrase, Ku could also prevent the reversal of the transposition reaction, a process termed dis-integration (Moores et al., 1995; Dotan et al., 1995).

Mammaliam Cells

Defects in the Ku-Associated DNA Repair System Lead to Reduced Infectivity By Retroviruses in Mammalian Cells To see whether Ku affects retrotransposon and retrovirus propagation in mammalian systems, the abilities of a mammalian retrovirus to integrate into the genome of mammalian cells that are proficient or deficient in the Ku-associated DNA repair apparatus were analysed. For these studies, a derivative of the Moloney murine leukaemia virus (Mo-MLV) was used to infect various rodent cell lines (to allow infection, the virus was "pseudotyped" with the vesicular stomatitis virus G protein, yielding supernatents of an approximate titer of $1 \times 10^7$; Burns et al., 1993; Hopkins, 1993; Yee et al., 1994; and references therein).

Various dilutions were used to infect sub-confluent monolayers of cell lines and, 48 hours after infection, the cells were fixed, stained for beta-galactosidase activity, and the resulting blue-coloured LacZ positive colonies were counted. Cells used in these studies were wild-type Chinese hamster ovary (CHO) cell line K1, their Ku80-deficient derivative xrs-6 (for example, Taccioli et al., 1994), XRCC4-deficient XR-1 cells (XRCC4 functions together with Ku in the DNA DSB repair pathway; Li et al., 1995; Critchlow et al., 1997; Grawunder et al., 1997), and wild-type mouse cell line 3T3.

Figure 7:
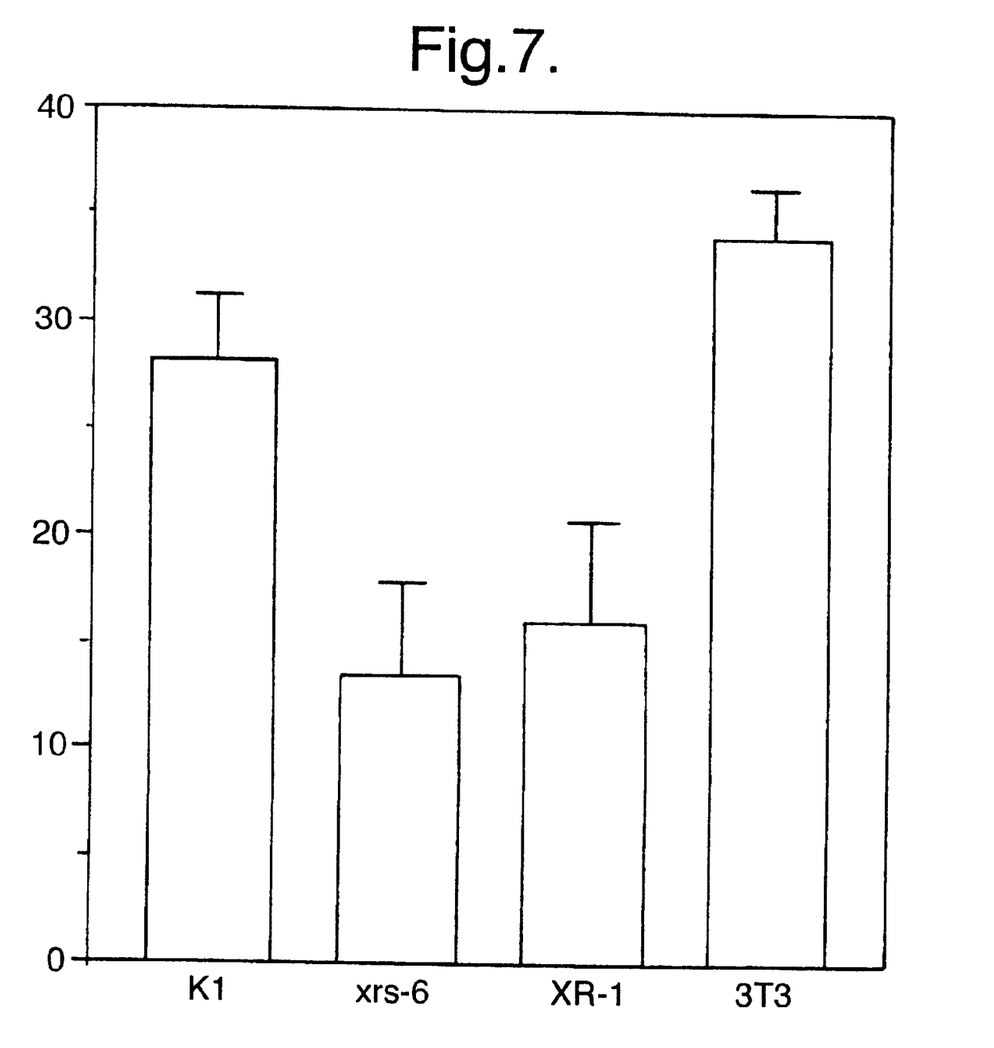
FIG. 7 shows the number of colonies of various cell types staining positive for β-galactosidase activity 48 hours after infection with VSV G glycoprotein pseudotyped MoMLV-based retroviral vector expressing LacZ.

As shown in FIG. 7, the cells deficient in Ku or XRCC4 generated significantly fewer blue colonies than the wild-type cells, indicating that Ku and XRCC4 indeed affect retroviral infection. Moreover, of the blue-staining colonies that did arise, those arising in the Ku-deficient or XRCC4-deficient cells contained significantly fewer blue-staining cells than was the case for the colonies arising in the wild-type cells. Therefore, in addition to decreasing the overall number of infected cell clones, the lack of Ku or XRCC4 also appears to either cause a delay in the division of infected cells or delays the retroviral integration process itself. Taken together, these data indicate that inhibition of Ku and its associated DNA repair components will indeed serve to inhibit retroviral infection in mammalian systems.

Given that this is also the case in yeast, it can be reasonably concluded that the requirement for the Ku-associated DNA repair apparatus in efficient retroviral and retrotransposon integration is ubiquitous throughout the eukaryotic kingdom.

In light of the above data, the involvement of other components of the mammalian Ku-associated DNA repair apparatus in efficient retroviral and retrotransposon integration may be established by assessing the efficiency of retroviral integration into cell lines deficient in other components of this system. For example, mouse, hamster and human cell lines exist that are deficient in the catalytic subunit of DNA-dependent protein kinase (DNA-PKcs), which is part of the Ku-associated DNA repair machinery in mammalian cells (see e.g. Blunt et al., 1995; Lees-Miller et al., 1995; for reviews, see Jackson and Jeggo, 1995; Jackson, 1996).

Where naturally occurring mammalian mutants do not already exist, targeted disruption of loci by standard "gene knock-out" approaches may be used to derive the desired cell type (eg. defective in mammalian ligase IV, or defective in homologues of yeast Rad50p, Mre11p, Xrs2p, Sir2p, Sir3p and Sir4p). Alternatively, studies may be performed in cells rendered deficient in repair due to the expression of dominant negative mutants of factors such as ligase IV, Rad50p, Mre11p, and Xrs2p. Since mammalian ligase III is very like ligase IV in sequence, cells deficient in ligase III or the associated XRCC1 protein may be tested for their ability to mediate retroviral or retrotransposon integration (the Chinese hamster ovary cell line derivatives EM-9 and EM-C11 lack functional XRCCL; Thompson et al. 1990; Caldecott et al. 1996; and references therein).

By using a variety of mammalian retrovirus types, it will also be straightforward to show that, as in yeast, the mammalian Ku-associated DNA repair apparatus plays an important role in the integration of a wide range of retrovirus into mammalian cells. Test viruses include other animal tumour retroviruses, human T-cell leukaemia viruses and HIV-1, which causes AIDS (HIV can be used to infect human cells or can be derivatised to infect rodent cells; eg. Naldini et al., 1996).

As described above for the yeast system, in vivo and in vitro studies may be employed to ascertain precisely at which step(s) the Ku-associated DNA repair machinery functions in mammalian retroviral and retrotransposon integration. Furthermore, already available assays may be used to define the roles performed by individual components of the machinery and define the precise regions of the various polypeptides that are critical for function. This should facilitate the design of assays for substances that disrupt this function and so are indicated for use as anti-retroviral agents.

Inhibitors of the Ku-Associated DNA Repair Apparatus Protect Against Retroviral Infection.

As described above for the yeast system, dominant negative derivatives of Ku subunits and other components of the Ku-associated DNA repair apparatus can be used to show that inhibition of this repair apparatus in normal cells results in decreased ability to stably integrate retrovirus into the host cell genome. For these studies, stable mammalian cell lines are generated that express the dominant negative mutant proteins. Wild-type mammalian cell lines are also treated with various drugs to show that this results in inhibition of retroviral integration.

In this regard, the compounds wortmannin and LY294002 have been shown to inhibit Ku-associated DNA-dependent protein kinase (DNA-PK) activity (Hartley et al., 1995; Vlahos et al. 1994; also unpublished data from the inventors' laboratory). Other DNA-PK inhibitors that are identified may be tested for effects. Although it is most simple to test agents initially on tissue culture cells, preliminary studies may subsequently be extended to involve animals such as mice (mice deficient or proficient in components of the Ku-associated DNA repair apparatus will be employed) and, ultimately, to human subjects.

Development of Assay Procedures For Agents That Reduce Retroviral Infectivity By Disrupting the Ku-Associated DNA DSB Repair Apparatus.

Determination of the mechanism by which the Ku-associated DNA repair machinery functions in retrovirus and retrotransposon integration facilitates design of assays that recapitulate these functions in defined in vivo or in vitro assays. Such assays are among those that may be used in screens for inhibitors, identifying substances as potential anti-retroviral agents.

Assays include those that measure full retroviral integration or just measure the step(s) of the process that are affected by the Ku-associated machinery. Although in vitro assays may be the easiest to employ in screens, yeast or mammalian cell lines may provide useful in vivo systems to test for effects. In this regard, human Ku70 and Ku80 may be expressed in yeast cells for assessment of Ty transposition or other aspects of Ku-dependent events. Such a "humanised" yeast system may be used to screen for molecules that interfere with human Ku function.

Another screen that may be used to identify novel anti-retroviral agents is one that identifies inhibitors of Ku-associated DNA-PK activity (for example, Dvir et al., 1992; Gottlieb and Jackson, 1993; Finnie et al., 1995; and references therein).

Other screens may be for compounds that inhibit enzymatic activities associated with ligases III or IV, Rad50p and Mre11p (both putative nucleases), interfere with protein-protein interactions within the Ku-associated repair apparatus (for example, between Ku and other components of the apparatus, between Rad50p, Mre11p and Xrs2p, between XRCC1 and ligase III, or between XRCC4 and ligase IV), or interfere with associations between the repair machinery and the DNA substrate. Peptides or peptide mimetics that resemble important regions of components of the Ku-associated repair system may be tested in addition to small molecule drugs.

Once identified through such routes, drugs (and their derivatives) may be tested in cell, animal and ultimately human systems for effects on retroviral and retrotransposon integration and on retroviral infection.

Other Applications For Activators or Inhibitors of the Ku-Associated DNA Repair Apparatus In addition to being of use in the identification and design of anti-retroviral drugs for use in vertebrate systems, activators or inhibitors of Ku-associated processes will also be of utility in other systems.

For example, retrotransposons are very abundant in the genomes of many higher plants and many transpose relatively frequently (Wessler, 1996). Indeed, much of the problematic somaclonal variation that occurs after plants are regenerated from protoplast tissue cultures appears to arise through retrotransposition events (Wessler, 1996). Aspects of the present invention may be used for suppressing the generation of somaclonal variation in plants by inhibition of the plant Ku-associated DNA repair apparatus.

REFERENCES

Alani, et al. (1989). *Genetics,* 122: 47–57.
Ausubel, et al. (1991). *Current Protocols in Molecular Biology* in K. Janssen J. Wiley & Sons,
Beall, et al. (1994). *Proc. Natl. Acad. Sci. USA,* 91: 12681–12685.
Blunt, et al. (1995). *Cell,* 80: 813–823.
Boeke, et al. (1985). *Cell,* 40: 491–500.
Boeke, J. D. and S. B. Sandmeyer. (1991). In *The Molecular and cellular biology of the yeast Saccharomyces* (ed. J. R.

Broach, J. R. Pringle, and E. W. Jones), pp 193–261. Cold Spring Harbor Laboratory Press. Cold Spring Harbor, N.Y., U.S.A.

Boulton, S. J. and Jackson, S. P. (1996). *EMBO*, 15: 5093–5103.

Boulton, S. J. and Jackson, S. P. (1996). *Nucl. Acids. Res.*, 24: 4639–4648.

Boulton, S. J. and S. P. Jackson. (1996). *EMBO J.*, 15: 5093–5103.

Bowerman, et al. (1989). *Genes Dev.*, 3: 469–478.

Brachmann, et al. (1995). *Genes Dev.*, 9: 2888–2902.

Braiterman, L. T. and Boeke, J. D. (1994). *Mol. Cell. Biol.*, 14: 5731–5740.

Brown, et al. (1987). *Cell* 49: 347–356.

Burns, et al. (1993). *Proc. Natl. Acad. Sci. USA.*, 90: 8033–8037.

Bushman, F. D. (1994). *Proc. Natl. Acad. Sci. USA.*, 91: 9233–9237.

Bushman, F. D. and R. Craigie (1991). *Proc. Natl. Acad. Sci. USA.*, 88: 1339–1343.

Bushman, et al. (1990). *Science*, 249: 1555–1558.

Cai, et al. (1994). *Cytogenet Cell Genet.*, 65: 221–227.

Caldecott, et al. (1996). *Nucl. Acids. Res.*, 24: 4387–4394.

Caldecott, et al. (1994). *Mol. Cell. Biol.*, 14: 68–76.

Caldecott, et al. (1995). *Nucl. Acid. Res.*, 23: 4836–4843.

Chan, et al. (1989). *J. Biol. Chem.*, 264: 3651–3854.

Chow, et al. (1992). *Science* 255: 723–726.

Craigie, et al. (1990). *Cell*, 62: 829–837.

Critchlow, et al. (1997). *Current Biology*, 7: 588–598.

Curcio, M. J. and D. J. Garfinkel (1991). *Proc. Natl. Acad. Sci. USA.*, 88: 936–940.

Dolganov, et al. (1996). *Molecular and Cellular Biology*, 16: 4832–4841.

Dotan, et al. (1995). *J. Virol.*, 69: 456–468.

Dvir, et al. (1992). *Proc. Natl. Acad. Sci. USA.*, 89: 11920–11924.

Dvir, et al. (1993). *J. Biol. Chem.*, 268: 10440–10447.

Eichinger, D. J. and Boeke, J. D. (1988). *Cell* 54: 955–966.

Eichinger, D. J. and Boeke, J. D. (1990). *Genes & Dev.*, 4: 324–330.

Falzon, et al. (1993). *J. Biol. Chem.*, 268: 10546–10552.

Feldmann and Winnacker (1993). *J. Biol. Chem.*, 268: 12895–12900.

Finnie, et al. (1995). *Proc. Natl. Acad. Sci. USA.*, 92: 320–324.

Fujiwara, T. and R. Craigie (1989). *Proc. Natl. Acad. Sci. USA.*, 86: 3065–3069.

Fujiwara, T. and K. Mizuuchi (1988). *Cell* 54: 497–504.

Garfinkel, et al. (1985). *Cell* 42: 507–517.

Gottlieb, T. M. and S. P. Jackson. (1993). i Cell, 72: 31–142.

Grandgenett, D. P., and Mumm, S. R. (1990). *Cell*, 60: 3–4.

Grawunder, et al. (1997). *Nature*, 388: 492–495.

Hartley, et al. (1995). *Cell*, 82: 849–856.

Hopkins, N. (1993). *Proc. Natl. Acad. Sci. USA.*, 90: 8759–8760.

Ivanov, et al. (1992). *Genetics*, 132: 651–664.

Jacoby and Wensink (1994). *J. Biol. Chem.*, 269: 11484–11491.

Jackson, S. P. and P. A. Jeggo. (1995). *Trends in Biochemical Sciences*, 20: 412–415.

Jackson, S. P. (1996). *Current Opinion in Genetics & Development}*, 6: 19–25.

Jackson, S. P. (1997). *Nature*, 388: 829–830.

Katz, et al. (1990). *Cell*, 63: 87–95.

Lee, M. S. and R. Craigie. (1994). *Proc. Natl. Acad. Sci. USA.*, 91: 9823–9827.

Lees-Miller, et al. (1995). *Science*, 267: 1183–1185.

Lewis, S. M. (1994). *Adv. Immunol.*, 56: 27–149.

Li, et al. (1995). *Cell*, 83: 1079–1089.

Mages, et al. (1996). *J. Biol. Chem.*, 271: 7910–7915.

Melamed, et al. (1992). *Mol. Cell. Biol.*, 12: 1613–1620.

Mellor, et al. (1985). *Nature*, 318: 583–586.

Milne, et al. (1996). *Mol. Cell. Biol.*, 16: 4189–4198.

Moore, S. P. and D. J. Garfinkel (1994). *Proc. Natl. Acad. Sci. USA.*, 91: 1843–1847.

Moore, et al. (1995). *J. Virol.*, 69: 4683–4692.

Naldini, et al. (1996). *Science*, 272: 263–267.

Nussenzweig, et al. (1996). *Nature*, 382: 551.

Paillard, S. and Strauss, F. (1991). *Nucleic Acids Res.*, 19: 5619–5624.

Petrini, et al. (1995). *Genomics*, 29: 80–86.

Porter, et al. (1996). *Nucleic Acids Research*, 24: 582–585.

Pryciak, (1992). *EMBO. J.* 11: 291–303.

Reeves and Sthoeger (1989). *J. Biol. Chem.*, 264: 5047–5052.

Sakai, et al. (1993). *J. Virol.*, 67: 1169–1174.

Sandstrom, P. A. and T. M. Folks. (1996). *BioEssays*, 18: 343–346.

Siede, et al. (1996). *Genetics*, 142: 91–102.

Shar, et al. (1997). *Genes Dev.*, 11: 1912–1924.

Sharon, et al. (1994). *Mol. Cell. Biol.*, 14: 6540–6551.

Taccioli, et al. (1994). *Science*, 265: 1442–1445.

Teo, et al. (1997). *EMBO J.*, 16: 4788–4795.

Thompson, et al. (1990). *Mol. Cell. Biol.*, 10: 6160–6171.

Tsukamoto, et al. (1996). *Nucl. Acids Res.*, 24: 2067–2072.

Tsukamoto, et al. (1997). *Nature*, 388: 900–903.

Varmus, H. (1988). *Science*, 240: 1427–1435.

Vlahos, et al. (1994). *J. Biol. Chem.*, 269: 5241–5248.

Wang, et al. (1995). *Genes Dev.*, 9: 509–520.

Wei, et al. (1995). *Mol. Cell. Biol.*, 15: 3206–3216.

Wessler, S. R. (1996). *Current Biology*, 6: 959–961.

Wilson, et al. (1997). *Nature*, 388: 495–498.

Yaneva, et al. (1989). *J. Biol. Chem.*, 264: 13407–13421.

Yee, et al. (1994). *Proc. Natl. Acad. Sci. USA.*, 91: 9564–9568.

Zhang, et al. (1995). *J. Virol.*, 69: 3675–3682.

Zhu, et al. (1996). *Cell*, 86: 379–389.

Zou, et al. (1996). *Genes. Dev.*, 10: 634–645.

What is claimed is:

1. A method of screening for an agent which is an inhibitor of retrovirus and/or retrotransposon activity, which comprises:

providing a substance which comprises a component of a Ku-dependent DNA repair pathway or a fragment of such component;

exposing the substance to a test compound;

determining interaction between the substance and the test compound whereby the test compound which interacts with said component or fragment thereof is identified; and determining the ability of said test compound which interacts with said component or fragment thereof to inhibit retrovirus and/or retrotransposon activity.

2. A method according to claim 1 wherein said component is Ku, or the Ku70 or Ku80 subunit thereof.

3. A method of screening for an agent which is an inhibitor of retrovirus and/or retrotransposon activity, which comprises:

providing first and second substances, the first substance comprising a first component of a Ku-dependent DNA repair pathway or a peptide fragment thereof able to bind a second component of the Ku-dependent DNA repair pathway, the second substance comprising a second component of the Ku-dependent DNA repair pathway or a peptide fragment thereof able to bind said first component, under conditions in which the components normally interact;

exposing the substances to a test compound;

determining interaction between the two substances in the presence of the test compound whereby the test compound which disrupts interaction between the two components is identified; and determining the ability of said test compound which disrupts interaction between the two components to inhibit retrovirus and/or retrotransposon activity.

4. A method of screening for an agent which is an inhibitor of retrovirus and/or retrotransposon activity, which comprises:

providing components of a Ku-dependent DNA repair pathway;

exposing the components of a pathway to a test compound under conditions which would normally lead to the activation of the Ku-dependent DNA repair pathway; and determining an end result that is indicative of activation of the Ku-dependent DNA repair pathway; whereby inhibition of that end result indicates inhibition of the Ku-dependent DNA repair pathway by the test compound and whereby the test compound which inhibits the Ku-dependent DNA repair pathway is identified; and determining ability of said test compound which inhibits the Ku-dependent DNA repair pathway to inhibit retrovirus and/or retrotransposon activity.

5. A method according to claim 1 which further comprises combining said agent with a pharmaceutically acceptable excipient.

6. A method according to claim 1 which further comprises providing said agent to a cell to inhibit retrovirus and/or retrotransposon activity.

7. A method according to claim 6 wherein the cells is not within a human or animal body.

8. An inhibitor of retrovirus and/or retrotransposon activity identified according to claim 7.

9. An inhibitor according to claim 8 whcih acts on Ku or the Ku70 or Ku80 subunit thereof.

10. A method according to claim 3 which further comprises combining said agent with a pharmaceutically acceptable excipient.

11. A method according to claim 4 which further comprises combining said agent with a pharmaceutically acceptable excipient.

12. A method according to claim 3 which further comprises providing said agent to a cell to inhibit retrovirus and/or retrotransposon activity.

13. A method according to claim 4 which further comprises providing said agent to a cell to inhibit retrovirus and/or retrotransposon activity.

14. An inhibitor of retrovirus and/or retrotransposon activity identified according to claim 3.

15. An inhibitor of retrovirus and/or retrotransposon activity identified according to claim 4.

* * * * *